United States Patent
Trejo et al.

(10) Patent No.: US 6,646,427 B2
(45) Date of Patent: Nov. 11, 2003

(54) DETERMINATION OF CHLORIDE CORROSION THRESHOLD FOR METALS EMBEDDED IN CEMENTITIOUS MATERIAL

(75) Inventors: David Trejo, College Station, TX (US); David R. Miller, Orange, CA (US)

(73) Assignees: MMFX Steel Corporation of America, Irvine, CA (US); The Texas A&M University System, College Station, TX (US)

(*) Notice: Subject to any disclaimer, the term of this patent is extended or adjusted under 35 U.S.C. 154(b) by 0 days.

(21) Appl. No.: 10/138,196

(22) Filed: May 1, 2002

(65) Prior Publication Data

US 2003/0011387 A1 Jan. 16, 2003

Related U.S. Application Data

(60) Provisional application No. 60/288,210, filed on May 2, 2001.

(51) Int. Cl.$^7$ ................. G01N 27/12; G01N 27/31; G01N 17/04; G01R 27/08
(52) U.S. Cl. ............... 324/71.1; 324/700; 324/713; 204/404; 205/775.5
(58) Field of Search .................. 324/700, 713, 324/71.1, 71.2; 422/53; 205/775.5, 776.5, 778.5, 734, 776; 204/404

(56) References Cited

U.S. PATENT DOCUMENTS

| | | | |
|---|---|---|---|
| 4,285,733 A | 8/1981 | Rosenberg et al. | |
| 4,574,545 A | 3/1986 | Reigstad et al. | |
| 4,668,541 A | 5/1987 | Fagerlund | |
| 4,831,324 A | 5/1989 | Asakura et al. | |
| 5,015,355 A | * 5/1991 | Schiessl | 204/404 |
| 5,084,680 A | * 1/1992 | Mitchell et al. | 324/559 |
| 5,698,085 A | 12/1997 | Yu | |
| 5,855,721 A | * 1/1999 | Monteiro et al. | 156/274.4 |
| 5,916,483 A | * 6/1999 | Burge et al. | 252/390 |
| 6,071,436 A | 6/2000 | Incorvia | |
| 6,132,593 A | * 10/2000 | Tan | 205/776.5 |
| 6,280,603 B1 | * 8/2001 | Jovancicevic | 205/775.5 |
| 6,281,671 B1 | * 8/2001 | Schiessl et al. | 324/71.1 |

* cited by examiner

Primary Examiner—Anjan K. Deb
(74) Attorney, Agent, or Firm—M. Henry Heines; Townsend and Townsend and Crew LLP (57) ABSTRACT

The chloride corrosion threshold of a metal embedded in a cementitious structure is determined in an accelerated manner by using an electric field to increase the rate of migration of chloride ion into the structure and monitoring the interface between the metal and the cementitious material to detect the onset of corrosion, then determining the chloride corrosion threshold, which is defined as the chloride content of the cementitious material once corrosion has begun. This determination can be performed over a time period of as little as 2 to 3 weeks rather than the months or years required by conventional chloride corrosion test procedures.

26 Claims, 3 Drawing Sheets

DETERMINATION OF CHLORIDE CORROSION THRESHOLD FOR METALS EMBEDDED IN CEMENTITIOUS MATERIAL

CROSS-REFERENCE TO RELATED APPLICATION

This application claims priority from United States provisional patent application No. 60/288,210, filed May 2, 2001, for all purposes legally capable of being served thereby. The contents of provisional patent application No. 60/288,210 are incorporated herein by reference in their entirety, as are all literature citations in this specification.

BACKGROUND OF THE INVENTION

1. Field of the Invention

This invention resides in the field of corrosion testing of steel and other metals, and the use of steel reinforcements and other metals embedded in concrete and cementitious material in general.

2. Description of the Prior Art

Concrete is widely used as a construction material due to the ease with which it can be transported, formed and applied as well as its durability and high compressive strength. Concrete has a low tensile strength, but is readily corrected by the use of steel reinforcing bars. Steel-reinforced concrete has been used successfully in roadways, bridges, parking structures, and other constructions where high tensile strength is needed. These constructions proved reasonably durable until the late 1960's, when premature concrete delamination and spalling, previously encountered only in coastal areas, began to occur in regions in the snow belt. This coincided with the increased use of deicing salts on roads and bridges, and one result was that reinforced concrete bridge decks in those regions began to require maintenance after as little as five years of service. It was ultimately recognized that the low performance was caused by corrosion of the reinforcing steel in the concrete due to the intrusion of small amounts of chloride into the concrete.

The cost of maintaining bridge decks is very high and rising, but the use of chloride-containing deicing salts is increasing as well. Alternative deicing agents such as calcium magnesium acetate are available, but the higher cost of these agents has prevented them from having a significant effect on the widespread use of chloride salts. Federal agencies such as the Structure Division of the Federal Highway Administration (FHWA) are thus continually seeking cheaper yet still effective ways of reducing the chloride-induced corrosion of steel-reinforced concrete structures.

Concrete and other cementitious materials are highly alkaline, due to the presence of a large amount of calcium hydroxide and small amounts of alkali elements such as sodium and potassium. The high alkalinity causes the embedded steel to form a thin film along its surface. The film, which may consist of an inner dense spinel phase ($Fe_3O_4/\gamma\text{-}Fe_2O_3$) in epitaxial orientation to the steel substrate and an outer layer of $\alpha$-iron oxyhydroxide ($\alpha$-FeOOH), protects the steel from chemical attack but is itself susceptible to attack by chloride ions. This exposes the underlying steel, rendering it vulnerable to attack by the oxygen and moisture present in the concrete at the concrete-steel interface. Analyses have shown that corrosive attack can occur both in the presence and absence of oxygen.

Methods of preventing or retarding the corrosion of steel-reinforcements have included the use of epoxy coatings over the steel reinforcement bars and the use of low-permeability concretes such as low water-cement ratio Portland cement concrete, latex-modified concrete, and other specialty concretes. The use of an increased concrete cover over the reinforcing steel has also been used, as have waterproof membranes and asphalt overlays. In general, however, coatings and overlays are either impractical or only serve to slow down the corrosion rate rather than stopping it entirely. Uncoated steel bars are still the most widely used.

Other materials are often embedded in concrete to serve a variety of functions. Examples are metallic conduits for conveying liquids, gases, or electricity. Water pipes, for example, which can be copper, brass of other non-ferrous metals as well as ferrous metals themselves are at times embedded in concrete and raise corrosion questions. Electrical conduits and wires for either transmitting electricity or grounding are also used and raise similar corrosion questions. In all cases, standardized testing methods for evaluating the chloride corrosion threshold are a useful means of evaluating the metals and the concrete in which they are embedded.

In the case of steel-reinforced concrete, it was reported in 1962 that the chloride corrosion threshold, which is defined as the lowest concentration of chloride in the concrete immediately surrounding the steel that will initiate corrosion of the steel, is 0.15 percent soluble chloride, by weight of cement. Lewis, D. A., "Some Aspects of the Corrosion of Steel in Concrete," *Proceeding of the First International Congress on Metallic Corrosion*, London, 1962, pp. 547–555. Studies at the FHWA laboratories in the mid-1970's led to an even lower estimate of the chloride corrosion threshold, this time expressed as total chloride, which includes both ionized and organic chloride. The FHWA estimate was 0.033 percent total chloride (again by weight of concrete). Berman, H. A., "The Effects of Sodium Chloride on the Corrosion of Concrete Reinforcing Steel and on the pH of Calcium Hydroxide Solution," Report No. FHWA-RD-74-1, Federal Highway Administration, Washington, D.C., 1974; Clear, K. C., "Time-to-Corrosion of Reinforcing Steel in Concrete Slabs," Report No. FHWA-RD-76-70, Federal Highway Administration, Washington, D.C., 1976. Raising the chloride corrosion threshold lowers the susceptibility of the steel to chloride-induced corrosion, and the value of the threshold has indeed been shown to vary with the type of cement or cementitious material and the mix proportions used, since these can entail differences, for example, in the concentrations of tricalcium aluminate and hydroxide ion.

The testing of the chloride corrosion of embedded uncoated steel is a valuable means of evaluating cementitious materials and cementitious material admixtures as well as the steel itself. This is also true for other embedded metals. Typical of the commonly used methods to test the chloride corrosion of embedded steel is ASTM G 109, "Standard Test Method for Determining the Effects of Chemical Admixtures on the Corrosion of Embedded Steel Reinforcement in Concrete Exposed to Chloride Environments," published by the ASTM Committee G-1 on Corrosion, Deterioration, and Degradation of Materials, Subcommittee G01.14 on Corrosion of Reinforcing Steel, published yearly to the present. This is a static test that entails repeated measurements at four-week intervals and typically over a year to complete. Such an extended time scale severely limits the rate at which new materials can be developed and investigated.

SUMMARY OF THE INVENTION

It has now been discovered that the chloride corrosion threshold of metal embedded in a cementitious structure can be determined in an accelerated manner by using an electric field to increase the rate of migration of chloride ions into the structure from an external liquid solution, monitoring an appropriate parameter at the interface between the embedded metal and the cementitious material to determine when corrosion has begun, and then determining the chloride content of the cementitious material at or very close to (i.e., within a few millimeters of) the interface. The electric field that accelerates the chloride ion migration is achieved by placing a chloride ion-containing liquid solution in contact with the structure and applying an electric potential between a cathode immersed in the solution and an anode embedded in the cementitious structure at a location in proximity to the embedded metal. The parameter that is used to detect the onset of corrosion is any of various electrical parameters that bear a known correlation to the corrosion rate. One such parameter is the electric potential at the interface of the metal and the cementitious material, which is monitored by connecting the embedded metal to electric circuitry as a working electrode and applying an electric potential between it and a counter electrode. Another is the polarization resistance, i.e., the slope of the potential vs. the applied current. Preferably, a reference electrode is included that is positioned within a few millimeters, most preferably within about one millimeter, from the interface, and the potential drop between the interface and the reference electrode is measured and expressed as the current density at the interface. A critical value of the current density is recognized as indicative of active corrosion of the metal.

This invention thus resides in a method for determining the chloride corrosion threshold of a steel reinforcement in steel-reinforced concrete and other cementitious material, or of any potentially corrodible metal embedded in a set mass of cementitious material, by the procedure described above. The invention also resides in apparatus for performing the determination, the apparatus including a mold for molding the cementitious material around a sample of the metal, a liquid reservoir or receptacle that can be adjoined to the mold such that the liquid contents of the reservoir are in contact with the cast cementitious material, and various electrodes and electrical connections that permit the electric potentials in the preceding paragraph to be applied and the measurements taken.

The method and apparatus of this invention are useful in obtaining an accelerated chloride corrosion test that can be performed over a time period of as little as 2 to 3 weeks rather than requiring months or years as do conventional chloride corrosion test procedures. The method and apparatus are also useful in comparing different steel alloys as reinforcement bars (or different metals in general), different cementitious material formulations, including the use of mineral and/or chemical admixtures, and different mixing and curing procedures. The information obtained from the practice of this invention can be used for analytical purposes in the development of new or existing materials of construction or as a means of comparing or predicting the service life of a reinforced concrete structure or any embedded metals in a concrete structure.

Other features, embodiments, objects, and advantages of the invention will become apparent from the description that follows.

DETAILED DESCRIPTION OF THE INVENTION

The terms "cementitious material" and "cementitious composition" are used herein interchangeably in the same manner in which these terms are used in the construction art. These terms denote any of various building materials that may be mixed with a liquid such as water to form a plastic paste, including aggregates in many cases. Examples of cementitious materials or compositions are cements, mortars, and concrete mixes, including neat paste compositions, oil well cement slurries, and grouting compositions. Preferred cementitious materials are hydraulic cements which are defined as pulverized, calcined argillaceous and calcareous materials that, when mixed with water, set and harden as a result of chemical reactions. A preferred cementitious material in the practice of this invention is mortar, which is a composite material that consists of a mixture of portland cement and water combined with particles or fragments of a relatively inert material filler, such as sand. Pozzolanic, pozzolanic-cementitious, or other admixture materials, such as condensed silica fume and fly ash, may also be included. Typical concrete mixes contain the following components, relative to 100 parts by weight of cement: about 160 to about 240 parts by weight of sand, about 120 to about 180 parts by weight of gravel, and from about 35 to about 60 parts by weight of water. Further information on the formulation and processing of concrete is found in the *ACI Manual of Concrete Practice, Part I*, published by the American Concrete Institute, Detroit, Mich., USA, 1995.

Testing in accordance with this invention is performed on set cementitious material. The term "set" is used herein to include the condition of the cementitious material at any stage from the initial set to the final cure, i.e., any stage at which the cementitious material has solidified into a unitary mass rather than a powder, paste, or slurry, even though further curing can continue over a succeeding span of months or even years.

The embedded metal or cementitious material that is tested in the practice of this invention may be any embedded metal or admixture to a cementitious system that is used or disclosed in the literature for use in concrete structures. The physical shape and dimensions of the embedded metal that is used in the test are not critical to the invention and may vary. For steel reinforced concrete, however, best results will be obtained when the sample is a section cut from the reinforcement stock that is actually intended to be used. The sample may thus be a cross-sectional slice of a steel rod across the axis of the rod, or any other such section that is conveniently cut from the reinforcement stock.

The metal can be bare or coated, since it may be desirable to test one or the other as a reinforcement material. This is true both of steel and of other metals.

In certain embodiments of the invention, the entire metallic sample will be tested, i.e., all surface areas of the sample will be exposed to the electric currents without the use of ion-impermeable coatings to shield parts of the surface of the sample. In other embodiments, however, when a more highly controllable and reproducible result is desired, the test will be focused on a designated portion of the surface area of the sample. A surface section of preselected size and dimensions on the sample can thus be designated as a test area by shielding other surface sections from ionic contact. This can be achieved by coating all sections other than the designated test area with an ion-impermeable coating such as an epoxy or other polymeric coating that shields the underlying metal from chloride or other chemical attack. Control of the location and dimensions of the test area in this manner will allow the area to be positioned transverse to the direction of the potential, which will help assure that chloride ion migration approaches the entire test area in a relatively uniform manner. The use of a designated test area also facilitates the determination of such area-based parameters as the current density, which is typically expressed in units of microamperes per square centimeter. The designated test area is preferably a region of the same surface of the reinforcement stock that is intended for contact with the cementitious material in field use, i.e., a surface section that has not been cut during preparation of the sample.

The inducement of chloride ion migration from the liquid solution to the embedded metallic sample is achieved by applying electric potential between a cathode in the solution and an anode embedded in the concrete at a location that places the sample in path of the ion flow. This is done without directly polarizing the sample (for example, by connecting the sample to the anode). The anode is preferably at the same level (i.e., the same distance from the cathode) as the sample, and when the sample is shielded by an ion-impermeable coating except for a designated test area, the anode is preferably at the same level as the test area. For curved test areas, which will be typical for steel reinforcement rods, the anode is preferably placed at any location that is level with any portion of the curvature. The anode may be ring-shaped to encircle the test area and thereby promote a uniform distribution of ion flow across the test area.

The migration path of the chloride ion from the liquid reservoir to the test area of the embedded metal may vary and is not critical to the invention, although a standardized path length should be used for purposes of comparison between test results. In preferred embodiments where the sample is masked except for a designated test area, the path length exceeds the longest dimension of the test area, most preferably at least twice the length of that dimension but not so long as to require excessive voltage to achieve the accelerated migration. In most applications, a path length ranging from about 10 mm to about 100 mm, preferably from about 25 mm to about 75 mm, will provide the best results. With path lengths of these ranges, the electric potential is preferably within the range of about 0.10 V to about 50 V, and most preferably within the range of about 1 V to about 25 V.

The monitoring of the interface between the metal and the cementitious material to determine when the chloride corrosion threshold has been reached is achieved by monitoring either the half-cell potential of the metal embedded in the cementitious material or any other corrosion-indicative parameter of the sample. A preferred method for evaluating the corrosion activity is the application of an electric potential between the sample and the counter electrode while measuring the current from the sample to obtain the polarization resistance. This measurement is preferably achieved by the use of a reference electrode that is placed in very close proximity to the test area on the sample. A particularly useful apparatus for reducing the influence of the resistance of cementitious material on the outcome of the test is a Luggin-Haber capillary, also known as a "Luggin probe," which is a capillary filled with a liquid electrolyte that is in fluid communication with a reservoir in which an electrode has been inserted. The reservoir is preferably an electrolyte-filled tube positioned external to the mold with the capillary extending from the tube through the wall of the mold into the cementitious material. The capillary is arranged so that its tip resides close to, but does not contact, the embedded metal sample. An ionically conducting path will thus exist between the capillary tip and the test area on the embedded metal without migration of the electrolyte. Best results will be obtained with a distance of less than 3 mm, preferably approximately 1 mm, between the capillary tip and the test area.

The liquid solution of chloride ion is any solution from which chloride ion will migrate under the influence of an electric field. The solvent can be any solvent in which a chloride salt will dissolve. Aqueous solutions are the most convenient and least costly. The chloride ion is typically supplied by a chloride salt, preferably an inorganic salt. The salt concentration is likewise not critical to the invention and can vary, although the use of a standardized concentration will permit comparisons and reproducibility as well as standardization. Alkali or alkaline each metal chlorides, such as sodium and potassium chlorides, are preferred, with sodium chloride especially preferred. Best results will generally be obtained with a chloride ion concentration of from about 0.5% to about 20%, preferably from about 1% to about 10%, by weight in water.

Independent electric circuits are preferably used for applying the two potentials, i.e., the potential used for inducing the chloride ion migration and the potential used for measuring the potential drop (or other suitable parameter) at the test area on the embedded metal for purposes of detecting the onset of corrosion. The potentials are not applied simultaneously; neither circuit is engaged while the other is in use. To achieve monitoring, therefore, the two circuits are engaged in alternating manner at certain stages of the procedure. In addition, it is preferable to apply the chloride migration potential for an initial series of incremental periods or pulses before taking the first measurement to check for active corrosion. The increments preferably range from about 8 hours to about 16 hours in duration, separated by intervals that are also from about 8 hours to about 16 hours in duration, and the first corrosion activity measurement is preferably taken after an initial period of from about 50 hours to about 75 hours of applied chloride migration potential. Measurements are then taken at periodic intervals. When the measured parameter that is indicative of the corrosion rate reaches a value that indicates active corrosion, the induced chloride migration is discontinued and the test is ended to permit analysis of the cementitious material in the vicinity of the test area for its chloride content. The corrosion rate is preferably expressed as current density, and in preferred embodiments of the invention, the critical value of the corrosion rate, i.e., the value corresponding to the chloride corrosion threshold, is a preselected value within the range of from about 1 $\mu A/cm^2$ to about 20 $\mu A/cm^2$. A typical chloride corrosion threshold is 10 $\mu A/cm^2$.

The cementitious material can be analyzed for its chloride content by methods that are known among those skilled in the art of the manufacture and analysis of structural concrete. The analysis is performed on a portion of the material that is in very close proximity to the embedded metal, preferably within 5 mm of the surface, and most preferably within 1 or 2 mm, and in the case of a steel or other metallic sample with a designated test area the analysis performed on a portion of the cementitious material in close proximity to the test area. According to one example of an analytical method, the material is pulverized, then digested with an acidic digestion solution, and the chloride content of the resulting solution is determined by use of a chloride-specific ion electrode. An example of this type of analytical method is published by the Strategic Highway Research Program in Report No. SHRP-S/FR-92-110 by P. Cady and E. Gannon, *Condition Evaluation of Concrete Bridges Relative to Reinforcement Corrosion, Volume 8. Procedure Manual,* 1992, in the section entitled "SHRP Product 2032: Concrete Deterioration Evaluation Manual," available from FHWA, Office of Technical Applications, Washington, D.C.

In aspects of the invention that address the apparatus used for the tests described above, the invention resides in an open-top mold in which the cementitious material is cast into a solid unitary block with a sample of the metallic material embedded in the block, together with a receptacle that forms a reservoir when placed in the open top of the mold to retain the chloride solution and place the solution in direct liquid contact with the block of cementitious material. The mold also includes electrical contacts and connections for applying an electric potential between the interior of the mold and the interior of the receptacle, as well as electrical contacts and connections for determining the potential drop and/or current density at the surface of the metallic sample when the sample is embedded in the cementitious material and an electric potential is applied across the surface of the sample. The mold and receptacle are preferably cylinders, with the receptacle cylinder sized to fit inside the open top of the mold cylinder. In certain preferred embodiments of the invention, the mold cylinder is a series of cylindrical sections whose rims are configured to permit the sections to be secured together coaxially to form a continuous cylinder stack, the contacting rims also being configured to allow electrical connections between electrodes inside the stack and external circuitry and electrical equipment such as a potentiostat and a power source. Further features of preferred apparatus within the scope of this invention are a counter electrode and a probe electrode such as a Luggin capillary, both mountable to the mold to extend into the mold interior with electrical leads passing through the mold walls for connection to external circuitry which is configured to measure the potential drop between the embedded steel and the probe electrode while a potential is applied between the embedded steel and the counter electrode. Still further features are an anode mountable to the mold to extend into the mold interior with leads passing through the mold wall, and a cathode for insertion into the receptacle for the chloride solution. Wire mesh or grid electrodes are preferred for the various electrodes.

Although this invention is of particular interest in its application to steel-reinforced concrete, it is applicable, as noted above to all corrodible metals embedded in cast cementitious materials, whether the metals be alloys, clad metals, coated metals, or pure metals, and regardless of the purpose that they serve once the mortar or concrete is cast around them.

The following example illustrates a test protocol that can be followed in the practice of the invention. This example is offered for purposes of illustration and is not intended to impose limits on the scope of the invention.

EXAMPLE

This example illustrates a procedure in accordance with the present invention for determining the critical chloride corrosion threshold level for uncoated steel reinforcement in a controlled mortar mix.

Equipment. The equipment used in this example included a Solartron SI 287 Potentiostat (20 V compliance) (Solartron Analytical, Farnborough, Hampshire, England) in conjunction with an Accumet #13-620-52 Calomel Reference Electrode (Fisher Scientific, Pittsburgh, Pa., USA), a power supply from a PROOVE' it Rapid chloride Permeability Test (Germann Instruments, Inc., Evanston, Ill., USA) (an alternative is Agilent Technologies E3611A Power Supply, Agilent Technologies, Palo Alto, Calif., USA), fine-mesh nickel-chromium wire gauze for the anode, cathode and counter electrode, solid copper wire (2.2 mm diameter) for attachment to the steel reinforcement sample, and a Luggin probe consisting of a glass tube approximately 150 mm in height and 15.5 mm inside diameter and a capillary approximately 40 mm in length and 2 mm inside diameter. The mold consisted of a plastic cylinder 75 mm in diameter and 115 mm in height, constructed in four sections, two of which were closed at one end, the others open at both ends. The chloride solution reservoir consisted of a plastic cylinder 50 mm in diameter and 50 mm in height, open at both ends.

The anode was prepared by cutting a piece of the wire mesh into a 70-mm diameter circular disk, and then cutting a 25-mm square from the center of the disk. A copper lead wire was soldered to the edge of the disk. The counter electrode was prepared by cutting a piece of the wire mesh into a 25-mm square and a copper lead wire was soldered to one side of the square.

Materials. The mortar components were cement, clean sand and water at weight ratios of 1:2:4.5 (water:cement:sand). The steel reinforcement tested was a 19-mm diameter reinforcing rod. A 0.1% aqueous NaCl solution was used as the reference electrode solution, and a 3.5% aqueous chloride solution was used as the source of chloride ion.

Figure 1A:
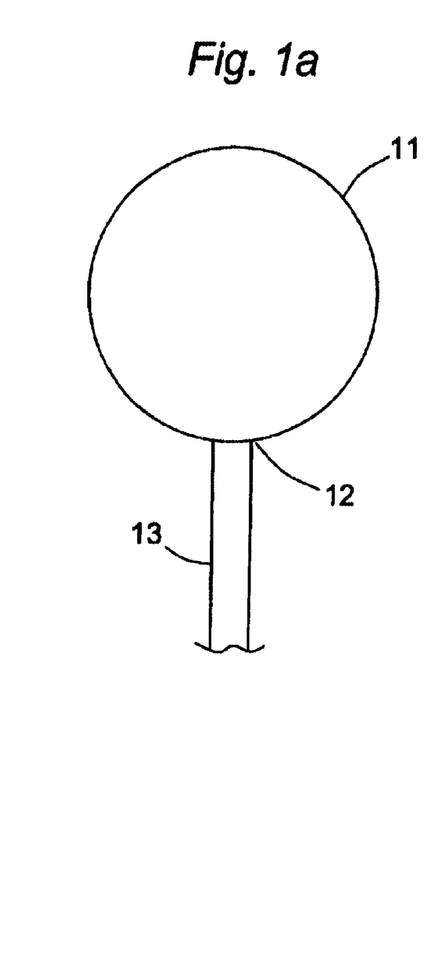
FIGS. 1a, 1b, and 1c, are an end view, side view and top view, respectively of a sample cut from a steel reinforcing rod, prepared for testing according to the procedure of the present invention.
Figure 1B:
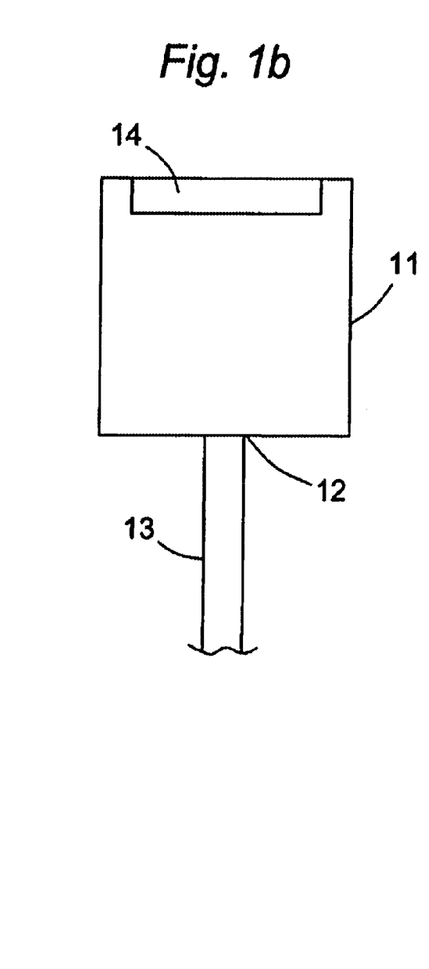
Figure 1C:
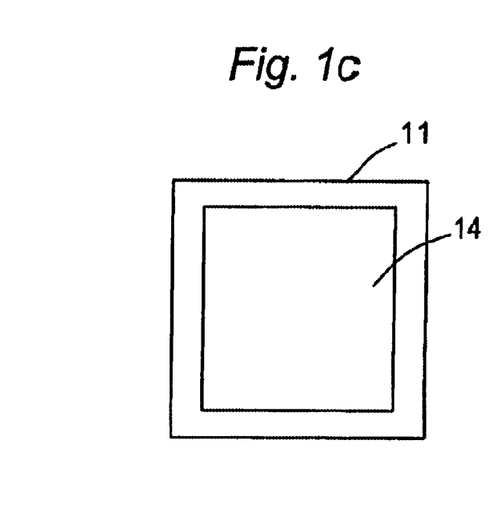

Preparation of the steel sample. The steel sample as prepared for testing is illustrated in FIGS. 1*a*, 1*b*, and 1*c*. The steel rod section 11 was a length of 19 mm cut from the reinforcement rod. In general, this is preferably done without damaging the steel surface around the perimeter of the cut and without causing excessive heat accumulation which may alter the steel microstructure. A hole 12, approximately 10 mm in depth, was drilled into the uncut (curved) surface of the sample and the hole was then threaded. The solid copper wire 13 was cut to an appropriate length governed by the desired height of cast concrete between the steel rod section and the chloride solution (this height is referred to hereinafter as the "cover"). Thus, for a cover of 50 mm, the copper wire was cut to a length of approximately 66 mm, and for a cover of 38 mm, the copper wire was cut to a length of approximately 78 mm. Each end of the wire was threaded, and one end was screwed into the steel rod section as shown in the views of FIGS. 1*a* and 1*b*. A base nut was placed on the other end not shown in FIGS. 1*a*, 1*b*, or 1*c*.

Figure 2:
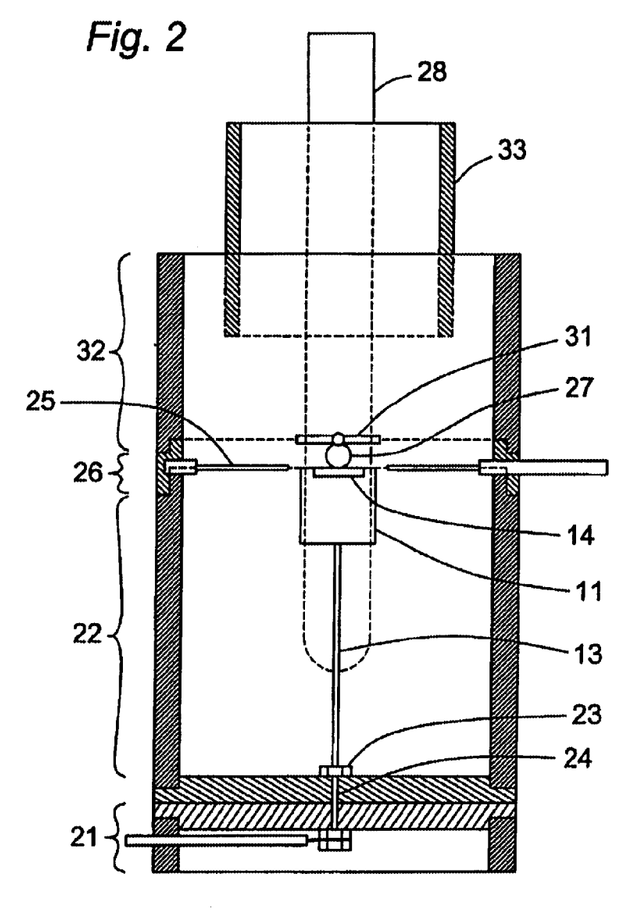
FIG. 2 is a diagram of a casting mold for use in testing the steel reinforcing rod sample of FIGS. 1a, 1b, and 1c.

The working electrode assembly (i.e., the rod section, wire, and base nut) was cleaned in ethyl alcohol with a sonic cleaner for approximately 5 minutes. An epoxy coating was applied to the entire working electrode assembly leaving only a test area 14 exposed on the curved surface of the rod section opposite the wire 13. This test area was rectangular in shape, measuring 13 mm×15 mm, 195 square millimeters. Once prepared in this manner, the working electrode assembly was mounted to the two lowermost sections of the mold as shown in FIG. 2, which shows the entire mold assembly.

The two lowermost mold sections 21, 22 were joined together with their closed ends facing each other and securing the base nut 23 of the working electrode assembly to a threaded electric lead 24 passing through the centers of the closed ends of the mold sections. The wire 13 of the working electrode assembly extended upward along the axis of the second cylindrical section 22, thereby positioning the steel rod section 11 so that the test area 14 was level with the open top of the second cylindrical section 22. The height of the second cylindrical section was thus equal to the total of the diameter of the steel rod section 11 and the length of the wire 13.

Casting of the concrete specimen while placing the electrodes. The mortar was prepared by mixing the cement, sand and water according to standard industry procedures as set forth in ASTM C192. Once prepared, the mortar was added to the second section 22 of the mold cylinder in two equal lifts and rodded approximately 20 times per lift to ensure consolidation of the mortar. The cylinder was tapped several times to allow entrapped air to escape to the exposed surface of the mortar. The exposed surface of the mortar was then struck even while keeping the test area free of excessive mortar.

The anode 25 was then positioned on the upper rim of the second cylindrical section 22 so that the test area 14 on the working electrode resided within the square opening of the anode. The third cylindrical mold section 26 (10 mm in length) was then fitted over the second section 22, securing the anode 25 between the contacting rims of the second and third sections. Mortar was then added to raise the mortar level to the top of the third cylindrical section 26. The Luggin probe capillary 27 and glass tube 28 were filled with the 0.1% aqueous NaCl solution, and the capillary 27 was inserted into a hole in the wall of the third cylindrical section to place the capillary tip approximately 1 mm from the test area 14 of the working electrode. The glass tube 28 of the probe was then taped (and later, after the concrete was set, secured by silicone) to the outside of the combined cylindrical sections.

The counter electrode 31 was then positioned on the exposed mortar surface over the test area, with the lead wire for the counter electrode passing over the exposed upper rim of the third cylindrical section 26. The fourth cylindrical section 32, measuring 30 mm in height, was then placed over the third cylindrical section 26 and filled with mortar. The exposed mortar surface was then leveled.

The cylinder to be used as the chloride solution reservoir 33 was centered on the exposed mortar surface and pressed and twisted into the mortar to a depth of approximately 6 mm. The sides of the uppermost cylindrical section 32 of the mold were tapped to reconsolidate the mortar around the reservoir. The mortar was then covered with moist clothes and plastic sheathing and allowed to set, then cured at 37±1° C. and 100% relative humidity for seven days. (Alternatively, a curing cycle of 14 days at 21° C. and 100% relative humidity or other humidity conditions can be used.)

Estimating the time for applied voltage and the test schedule. For a typical mortar mixture and operating conditions including a cover (mortar height above the test area) of 38 mm and 20 V of applied potential, the cumulative time of applied voltage required to reach the threshold at the test area interface can be estimated as follows when an approximate value of the critical chloride threshold is known. When the critical chloride threshold (expressed in pounds of chloride per cubic yard of concrete or mortar, depending on which is being used in the test) is estimated to be less than 1.2, the estimated time (in hours) of applied voltage to reach the threshold is the estimated threshold value divided by 0.015. When the threshold is estimated to be greater than 1.5, the estimated time of applied voltage to reach the threshold is obtained by adding 25.5 to the estimated threshold value and dividing the total by 0.27.

Figure 3:
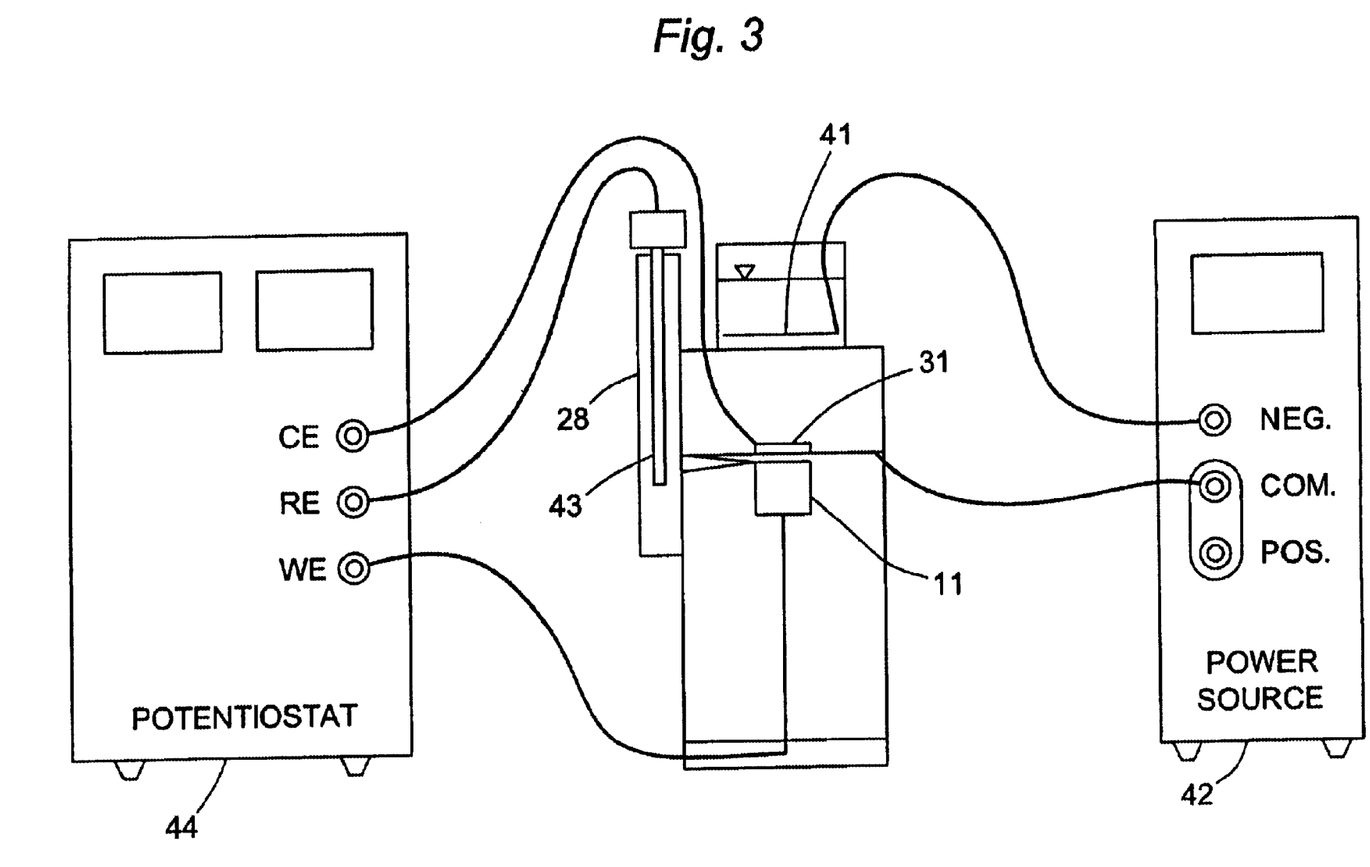
FIG. 3 is a diagram of the casting mold of FIG. 2 and the electrical systems to which the mold and its components are connected for performing a procedure in accordance with the present invention.

Test Procedure. The mold containing the mortar was placed on a flat surface near the power source and the potentiostat. The reservoir was filled to approximately 75% capacity with the 3.5% aqueous NaCl solution, and the cathode was placed in the reservoir. The reservoir was refilled with fresh solution after every applied potential period, and any salt that had precipitated on the inside wall of the reservoir was redissolved in the solution. Appropriate electrical connections were made as shown in FIG. 3. The cathode 41 and anode 25 were connected to the power supply 42 and the working electrode (steel rod section 11), counter electrode 31 and reference electrode 43 (located inside the glass tube 28 of the Luggin probe) were connected to appropriate terminals (labeled WE, CE, and RE, respectively, of the potentiostat 44. An open circuit potential of the working electrode was taken on the potentiostat either for 2 minutes or until stability was indicated. A scan by the potentiostat of −0.015 V to +0.015 V at a scan rate of 0.1667 mV/sec was taken vs. the open circuit potential to determine the polarization resistance $R_p$ in ohms, which was then converted to the corrosion rate in microamperes per square centimeter by multiplying the inverse of the polarization rate by 0.026. This was done at the beginning of the test before any voltage was applied by the power source, and periodically through the course of the test, as explained below.

A potential of 20 V between the cathode and anode was applied by the power supply in five 12-hour increments separated by 12-hour intervals. The fifth increment was followed by a 60-hour period with no applied potential. The polarization rate was then determined, and voltage was again applied between the cathode and anode at the same voltage level as before but for only 6 hours, followed by 42 hours of rest. The cycle of polarization rate determination, 6-hour voltage, and 42-hour rest period was then repeated until the corrosion rate exceeded 10 $\mu A/cm^2$. The chloride determination was then performed.

Determining the chloride content. The chloride reservoir cylinder was cut from the top of the mold, and the concrete in the mold was ground in increments to obtain a depth increment adjacent to the test area on the embedded steel rod section. Grinding was performed with an 18 mm-diameter diamond grinding bit positioned in a grinding machine held against the surface by a grinding plate. The section used for testing was obtained from an increment 1 mm deep at the test area interface and 35 mm in diameter. The resulting powder was collected with a vacuum device and 0.8 $\mu m$ filter.

The powder was suspended in 20 mL of a digestion solution prepared by combining 94 parts of distilled water, 6 parts of glacial acetic acid, and 5 parts of isopropyl alcohol (all by weight). Digestion was continued for 3 minutes, after which time 80 mL of a stabilizing solution prepared by combining 4 parts of a 0.1545 g/L aqueous NaCl solution with 96 parts of distilled water (all by volume) was added with agitation for 1 minute. A chloride ion specific electrode, appropriately calibrated, was then placed in the resulting solution. The electrode was an Orion Combination Chloride Electrode Model 96-17B with chamber filling solution no. 900017 and an Orion Model 250A Multimeter (Thermo Orion Division of Thermo Electron Corporation, Beverly, Mass., USA). The percent chloride in the sample was then calculated by the relation $$log_{10}(Cl^- \text{ in } ppm) = C + [D \times (\text{electrode reading in } mV)]$$

in which C and D are constants determined in the calibration step. Typical values of these constants are 2.855 and −0.01835, respectively.

The foregoing is offered primarily for purposes of illustration. Modifications of the particular arrangements of the components, the steps of the procedure, the operating conditions and other system parameters, as well as substitutions of components and other aspects of the method and apparatus described above that nevertheless embody the spirit and underlying concepts of the invention and thereby still fall within its scope will be readily apparent to those skilled in the art.

What is claimed is:

1. A method for determining the chloride corrosion threshold of metal embedded in a cementitious material, said method comprising:

(a) encasing a sample of said metal in a set mass of said cementitious material in which are embedded components comprising an anode, a counter electrode and electrical leads capable of individually joining said metallic sample, said anode and said counter electrode to electrical circuitry external to said mass, (b) placing a liquid solution of chloride ions in contact with said set cementitious material, with a cathode immersed in said liquid solution;

(c) applying in time increments an electric potential between said cathode and said anode to induce migration of chloride ions from said liquid solution through said set cementitious material to said metallic sample, without directly polarizing said sample;

(d) between time increments of step (c), determining the half-cell potential of said metallic sample or applying an electric potential between said metallic sample and said counter electrode while detecting the value of a parameter indicative of the presence or absence of corrosion activity of said metal at an interface between said metallic sample and said set cementitious material; and (e) analyzing said set cementitious material for chloride content at a location adjacent to said metallic sample at a time corresponding to the point at which the half-cell potential or corrosion activity indicated by said detected value exceeds a selected critical level, said chloride content thus detected representing said critical chloride threshold.

2. A method in accordance with claim 1 in which step (d) comprises applying an electric potential between said metallic sample and said counter electrode while detecting the value of a parameter indicative of the presence or absence of corrosion activity of said metal at an interface between said metallic sample and said set cementitious material.

3. A method in accordance with claim 1 in which said components embedded in said set mass of cementitious material further comprise a liquid electrolyte-filled probe positioned within 3 mm of said interface between said metallic sample and said set cementitious material and arranged to function as reference electrode, and step (d) comprises applying an electric potential between said metallic sample and said counter electrode while detecting an electrical potential between said interface and said liquid electrolyte-filled probe.

4. A method in accordance with claim 1 in which said anode is shaped and positioned to encircle said metallic sample.

5. A method in accordance with claim 2 in which said parameter of step (d) is polarization resistance.

6. A method in accordance with claim 1 in which said liquid solution of chloride ions is an aqueous chloride solution.

7. A method in accordance with claim 1 in which said liquid solution of chloride ions is an aqueous sodium chloride solution.

8. A method in accordance with claim 2 in which said selected critical level of said corrosion rate, expressed in current density, is a selected value within the range of from about 1 $\mu A/cm^2$ to about 20 $\mu A/cm^2$.

9. A method in accordance with claim 2 in which said selected critical level of said corrosion rate, expressed in current density, is 10 $\mu A/cm^2$.

10. A method in accordance with claim 1 in which step (b) comprises placing said liquid solution in contact with said set cementitious material such that said liquid solution and said metallic sample are separated by from about 10 mm to about 100 mm of said set cementitious material.

11. A method in accordance with claim 1 in which step (b) comprises placing said liquid solution in contact with said set cementitious material such that said liquid solution and said metallic sample are separated by from about 25 mm to about 75 mm of said set cementitious material.

12. A method in accordance with claim 1 in which step (e) comprises analyzing a portion of said set cementitious material located within 5 mm of said interface between said metallic sample and said set cementitious material.

13. A method in accordance with claim 1 in which said electric potential of step (c) is from about 0.10 V to about 50 V.

14. A method in accordance with claim 1 in which said electric potential of step (c) is from about 1 V to about 25 V.

15. A method in accordance with claim 1 in which each of said time increments of step (c) are from about 8 hours to about 16 hours in duration, separated by intervals of from about 8 hours to about 16 hours in duration.

16. A method in accordance with claim 15 in which step (d) comprises comprises applying an electric potential between said metallic sample and said counter electrode while detecting the value of a parameter indicative of the presence or absence of corrosion activity of said metal at an interface between said metallic sample and said set cementitious material, and detecting said value of said parameter after an initial period of from about 50 hours to about 75 hours of potential applied between said cathode and said anode and at periodic intervals thereafter.

17. A method in accordance with claim 1 in which said metal of said metallic sample is steel.

18. A method in accordance with claim 1 in which said cementitious material is mortar and said metal of said metallic sample is steel.

19. Apparatus for the determination of the chloride corrosion threshold of a metal embedded in cementitious material, said apparatus comprising:

a mold having an open top to receive cementitious material and a sample of said metal and to allow said cementitious material to set into a solid unitary block with said metallic sample embedded therein;

a receptacle capable of retaining liquid and shaped to be placed in communication with said open top of said mold in such a manner that when liquid is retained in said receptacle and a solid unitary block resides in said mold, said liquid contacts said solid unitary block;

means for applying an electric potential between the interior of said mold and the interior of said receptacle; and means for determining current density at the surface of a metallic sample in said mold when an electric potential is applied across said surface.

20. Apparatus in accordance with claim 19 in which said mold is a first cylinder open at one end and said receptacle is a second cylinder sized to fit inside said open end of said first cylinder.

21. Apparatus in accordance with claim 19 in which said mold is a series of cylinders having rims contoured to secure said cylinders together coaxially in a stack, and said means for applying an electric potential and for determining current density comprise electrodes insertable into said mold between the rims of adjacent cylinders.

22. Apparatus in accordance with claim 19 in which said means for determining current density consist of:

a counter electrode and a reference electrode, both mountable to said mold to extend into the interior of said mold, and means for measuring potential drop between said metallic sample and said reference electrode while applying an electric potential between said metallic sample and said counter electrode.

23. Apparatus in accordance with claim 19 in which said means for applying an electric potential between the interior of said mold and the interior of said receptacle comprise a first electrode mountable to said mold to extend into the interior of said mold and a second electrode mountable to said receptacle to extend into the interior of said receptacle, and means for connecting said first and second electrodes to a voltage source as anode and cathode, respectively.

24. Apparatus in accordance with claim 19 in which said means for determining current density consist of:

a counter electrode and a reference electrode, both mountable to said mold to extend into the interior of said mold, and means for measuring potential drop between said metallic sample and said reference electrode while applying an electric potential between said metallic sample and said counter electrode, and said means for applying an electric potential between the interior of said mold and the interior of said receptacle comprise:

an anode mountable to said mold to extend into the interior of said mold and a cathode mountable to said receptacle to extend into the interior of said receptacle, and means for connecting said anode and cathode to a voltage source.

25. Apparatus in accordance with claim 24 in which said counter electrode and said anode are wire mesh electrodes.

26. Apparatus in accordance with claim 24 in which said counter electrode, said anode and said cathode are wire mesh electrodes.

* * * * *